United States Patent [19]

Loescher et al.

[11] Patent Number: 5,496,739
[45] Date of Patent: Mar. 5, 1996

[54] TEST FOR GLYCOL IN WATER

[75] Inventors: Barry R. Loescher, Barrie; David M. Newman; Rodney D. Thomson, both of Burlington, all of Canada

[73] Assignee: Zenon Airport Environmental Inc., Burlington, Canada

[21] Appl. No.: 207,013

[22] Filed: Mar. 4, 1994

[51] Int. Cl.$^6$ .................................................. G01N 33/00
[52] U.S. Cl. ...................... 436/131; 436/132; 436/139; 436/166; 436/61
[58] Field of Search ..................... 436/131, 132, 436/139, 40, 60, 61, 164, 166; 422/57, 56

[56] References Cited

U.S. PATENT DOCUMENTS

| | | | |
|---|---|---|---|
| 2,452,385 | 10/1948 | Merckel | 422/57 |
| 2,800,460 | 7/1957 | Grosskopf | 436/139 |
| 3,436,188 | 4/1969 | Boyd et al. | 436/40 |
| 3,635,677 | 1/1972 | Drake et al. | 436/60 |
| 3,700,409 | 10/1972 | Zall | 436/139 |
| 3,784,358 | 1/1974 | Drake, Jr. | 422/56 |
| 4,125,373 | 11/1978 | Scoggins | 436/60 |
| 4,272,479 | 6/1981 | Huneke et al. | 422/57 |
| 4,731,332 | 3/1988 | Blumenthal et al. | 435/61 |

FOREIGN PATENT DOCUMENTS

| | | |
|---|---|---|
| 1018878 | 10/1977 | Canada . |
| 207580 | 5/1982 | German Dem. Rep. . |
| 1269009 | 1/1985 | U.S.S.R. . |

OTHER PUBLICATIONS

Latif et al, Chemical Oxygen demand of Starches and related product, 1992, Sci, Int (Lahore) (1992), 4(4), 351–3.
Shriner et al, The Systematic Identification of Organic Compounds, 6th Ed, 1980, pp. 149–150.
Gudernatsch et al, A rapid determination of COD without addition of mercuric sulfate, Z. Wasser Abwasser Forsch, 1975, 8(6)182–4.
Leithe, Determining the chemical oxygen demand in diluted effluents, Wasser, Luft Betr. (1970), 14(2), 55–6.
Ruzicka et al, Determination of the oxidizability of tannery waste waters by a dichromate method, Kozarstvi (1969) 19(7), 164–8.
Nuysink et al, The effect of polyethylene oxide molecular weight on determination of its concentration in aqueous solution Talanta (1982), 29(6), 495–501.
Ballarin, Studies on the identification of Pharmacopeial glycols by thin–layer chromatography, Ingenieursch. pharm Prax (1980), 35(6), 260–4.
Gardner, Field colorimetric determination of fuel system icing inhibitor (ethylene glycol mono methyl ether) J. Inst. Petrol, London (1971), 57(557), 294.
Nisbet et al, Rapid detection and estimation of polyol humectant in tobacco by thin layer chromatography, Tob. Sci. (1969), 13, 109–10.
Smirnova et al, Determination of free polyethylene glycols in oxyethylated products. Zavod. Lab (1978), 44(1), 26–8.
Friedrich et al, Formation of ethylene chlorohydrin and ethylene glycol on gas treatment of Senna pods with ethylene oxide Arch. Pharm ( Weinbeim, Ger) (1977), 310(5), 363–8.
Standard Methods for the Analysis of Water and Wastewater, 7th Edition, Chemical Oxygen Demand, 5220A–D, pp. 5–6 to 5–10.

*Primary Examiner*—James C. Housel
*Assistant Examiner*—Harold Y. Pyon
*Attorney, Agent, or Firm*—Andrew Alexander

[57] ABSTRACT

Disclosed is a method of determining the presence of glycol in an aqueous solution comprising providing a container containing a mixture of potassium dichromate, a catalyst comprised of mercuric sulfate and silver sulfate, the mixture provided in an acidic solution. To the container is added a controlled volume of aqueous solution containing glycol. The mixture is permitted a time sufficient to change color, the time not being in excess of 15 minutes. The color is compared to a set of color standards to determine the presence of glycol in said aqueous solution.

16 Claims, No Drawings

TEST FOR GLYCOL IN WATER

BACKGROUND OF THE INVENTION

This invention relates to a test that determines the amount of glycol in water such as runway surface water, and more particularly, this invention relates to a method and apparatus for quickly determining the amount of glycol contained in water.

Because of the increasing amount of air travel, there is ever-increasing pressure to fly aircraft in the wintertime. Attempting to maintain winter schedules often results in aircraft departures during snow storms. Accumulation of snow on the wings and body of the craft can interfere with lift. Thus to prevent such accumulations, the aircraft is sprayed at a spray pad or departure gate with a de-icing material containing glycol. While a large portion of the glycol-based material can be contained at the spray pad, a portion of it gets carried onto the runway and finds its way to storm drains. However, release of glycol to the environment is severely restricted by environmental protection agencies. Thus, to prevent such releases, the runways can be cleaned to recover the de-icing liquid prior to its entering the storm drains. Often, prior to cleaning or after cleaning, it is necessary to know the amount of glycol in the surface water on the runway to determine if cleaning is necessary or if further cleaning should be performed to prevent release of the glycol. This requires a test that can be performed out on the runway for purposes of immediate decisions. Prior procedures for glycol determination have not permitted such determination without a great deal of time to run the analysis. That is, the procedures have reverted to laboratory conditions where the organic material is oxidized in a boiling mixture of chromic and sulfuric acid, for example, as described in *Standard Methods for the Analysis of Water and Wastewater*, 7th Ed., on the basis of chemical oxygen demand (COD). The methods described therein in are an "Open Reflux Method" procedure 5220B and a "Closed Reflux, Tetrimetric Method", procedure 5220C. Both methods are complicated and as a result are usually carried out in an equipped laboratory.

In the prior art, there are disclosed tests for the determination of glycols. For example, Canadian Patent 1,018,878 discloses a method for testing for the presence of glycol-based antifreeze in lubricating oils using pellets containing $Na_2SO_3$, pararosaniline hydrochloride, $NaHCO_3$, magnesium stearate and polyvinylpyrrolidone. Generally, in the test, an oil sample is combined with toluene. A sample of the toluene/oil mixture is then added to a $H_2SO_4/KIO_4$ solution and after stirring, a pellet is added to this mixture. The amount of glycol present is indicated by color.

U.S. Pat. No. 3,635,677 discloses a procedure for the determination of glycol in oil. A sample of engine oil is added to an aqueous oxidizing solution and the mixture shaken and allowed to separate. A sample of the aqueous phase is added to a chromogenic aldehyde reagent adsorbed on a support media. The presence of glycol is observed by chromogenic determination.

U.S. Pat. No. 4,125,373 also discloses a method for determining the amount of trace ethylene glycol in oil.

However, none of these references provide for a quick determination of the amount of glycol in water. Further, these methods appear to require highly skilled technicians. Thus, it can seen that there is a great need for a quick test to determine the presence of glycol in water, such as surface water, in order that cleaning operations can be carried out efficiently.

SUMMARY OF THE INVENTION

It is an object of the invention to provide a test capable of determining the presence of glycol in an aqueous-based solution.

It is another object of the invention to provide a quick test capable of determining the presence of glycol in water.

It is still another object of the invention to provide a quick test capable of determining the presence of glycol in water that can be performed in the field by a relatively unskilled technician.

Yet, it is another object of the invention to provide a method and apparatus for determining the presence of glycol in water.

These and other objects will become apparent from a reading of the specification and claims appended hereto.

In accordance with these objects, there is provided a method of determining the presence or absence of glycol in an aqueous solution, the method comprising providing a container containing a mixture of potassium dichromate, a catalyst comprised of mercuric sulfate and silver sulfate, the mixture provided in an acidic solution comprised of a non-complexing acid. To the container is added a controlled volume of aqueous solution containing glycol. The mixture is permitted a time sufficient to change color, the time not being in excess of 15 minutes. The color is compared to a set of previously determined glycol in water color standards to determine the presence of glycol in the aqueous solution.

DETAILED DESCRIPTION OF THE PREFERRED EMBODIMENTS

The present invention is used to determine the presence or absence of glycol in a water solution. Also, the invention can be used to determine the approximate amount of glycol in the aqueous solution. The invention utilizes a strong oxidizing agent that in the presence of catalysts in an acidic solution will oxidize the glycol. Further, the invention is based on the fact that a color change accompanies the reduction in oxidation state of one of the species. Additionally, it is important that the presence of glycol in the water can be measured quickly.

For purposes of the present invention, the strong oxidizing agents are selected from potassium dichromate ($K_2Cr_2O_7$) and sodium dichromate ($Na_2Cr_2O_7$). The preferred oxidizing agent is potassium dichromate.

Catalysts suitable for the present invention are selected from the group consisting of mercuric sulfate ($HgSO_4$) and silver sulfate ($Ag_2SO_4$).

With respect to the acid, any strong, non-complexing acid or combination of acids can be used that permits the oxidation of the glycol and the change of color to occur. Thus, preferably the acid is selected from sulfuric acid, nitric acid and perchloric acid, with sulfuric acid having been found to be highly suitable. By non-complexing acid is meant an acid that will not react or combine strongly with the mercury, silver or chromium reagents and interfere with the test.

The test solution composition for determining the presence of glycol in water can comprise 0.0001 to 20 wt. % potassium dichromate, 0.01 to 3.2 wt. % mercuric sulfate, 0.0001 to 6 wt. % silver sulfate, the balance comprising acid (Composition I).

The acid used is preferably sulfuric acid. The composition preferably comprises 0.02 to 20 wt. % potassium dichromate, 0.001 to 2 wt. % mercuric sulfate, 0,001 to 3 wt. % silver sulfate, the balance acid (Composition II).

The composition can be used or adjusted to determine the presence of glycol in water in the range of about 30 to 10,000 ppm glycol.

A typical composition range for determining 30 to 1,50.ppm glycol in water is 0.0025 to 0.25 wt. % potassium dichromate, 0.001 to 2 wt. % mercuric sulfate, 0.001 to 3 wt. % silver sulfate, the balance acid (Composition III).

A typical composition range for determining the presence of about 150 to 1500 ppm glycol in water is 0.25 to 1 wt. % potassium dichromate, 0.001 to 5 wt. % mercuric sulfate, 0.001 to 6 wt. % silver sulfate, the balance acid (Composition IV).

The acid preferably is sulfuric acid. The sulfuric acid can have a molarity in the range of 1 to 18 molar, or the acid can have a concentration in the range of 40 to 99 wt. % $H_2SO_4$. Thus, a solution for testing for the presence of glycol in water is prepared by adding the above salt composition to sulfuric acid, or like acid, to provide a solution containing 0.001 to 10 wt. % of the salt composition, the sulfuric acid having a concentration in range of 1 to 18 M.

Preferably, the test composition or solution and glycol containing aqueous solution are added to provide a mix containing 0.25 to 10 parts, preferably 0.25 to 5, test solution to one part glycol containing aqueous solution,, with typical mixes comprising 0.5 to 2 parts test solution to one part glycol containing aqueous solution.

After the solution has been prepared, 5 ml. can be added to a test tube and 1 ml. of glycol containing water can be added to the test tube. The two solutions are mixed thoroughly and then permitted to react for 1 to 15 minutes, preferably 1 to 5 minutes and typically 1 to 3 minutes, to develop color. The color is then compared to standard colors for given glycol concentrations in water using controlled amounts of test solution.

A controlled amount, e.g., 5 to 10 ml, of the test solution can be packaged in clear vials or test tubes that permit the addition of a controlled amount of water containing glycol to added to the vial or test tube.

For purposes of testing, it is preferred that the color development be achieved quickly. Thus, preferably, comparison for color can be accomplished in less than 15 minutes, more preferably less than 10 minutes and typically less than 5 minutes.

Thus, it will be seen that the invention has the advantage that determination for the presence of glycol can be quickly and efficiently performed in the field by relatively unskilled laboratory technicians.

By the term glycol as used herein is meant to include all types of glycol including ethylene glycol, propylene glycol and diethylene glycol.

The following example is further illustrative of the present invention.

EXAMPLE

Samples of water runoff were taken from different areas of a commercial airport in January 1994. Each sample was 1 ml and it was added to 1 ml of a low concentration test composition. This test was repeated using a high concentration test composition. The low concentration test composition contained a mixture having 0.05 wt. % potassium dichromate, 0.08 wt. % mercuric sulfate and 0.3 wt. % silver sulfate in 1 ml of 98 wt. % sulfuric acid. The high concentration test composition contained a mixture having 0.5 wt. % potassium dichromate, 0.8 wt. % mercuric sulfate and 0.3 wt. % silver sulfate in 1 ml of 98 wt. % sulfuric acid. The results are provided in the Table. From the Table, it will be seen that for Sample SW1, the low concentration test indicated greater than 150 mg/l glycol and the high concentration indicated less than 500 mg/l glycol. This was confirmed by gas chromatography (GC) which showed 288.1 mg/l of total glycol. Similar results were obtained for the other Samples. The gas chromatography gave results for propylene glycol (PG), ethylene glycol (EG) and diethylene glycol (DG).

TABLE

Results-Field Testing, Quick Test Kit

| Sample | Description | Low Concentration Quick Test Results (mg/l) | High Concentration Quick Test Results (mg/l) | GC Results | | | |
|---|---|---|---|---|---|---|---|
| | | | | PG (mg/l) | EG (mg/l) | DG (mg/l) | Total (mg/l) |
| SW1 | Gate 106 Pounding Area | >150 | <500 | >5 | 270.8 | 9.3 | 288.1 |
| SW2 | Gate 104 Pounding Area | ~50 | — | >5 | <5 | 18.8 | 18.8 |
| SW3 | Gate 113 Pounding Area | ~100 | — | >5 | 90.1 | 20.6 | 110.7 |
| SW3 | Gate 113 Pounding Area | ~100 | — | — | — | — | — |
| SW4 | T2 Diversion Vault | >150 | >1500 | — | 6100 | — | 6100 |
| SW5 | W1 Diversion Vault | >150 | >1500 | — | 3700 | — | 3700 |
| SW6 | Alpha Pad Diversion Vault | — | >1000 and <1500 | — | 792 | — | 792 |

While the invention has been described in terms of preferred embodiments, the claims appended hereto are intended to encompass all embodiments which fall within the spirit of the invention.

Having thus described the invention and certain embodiments thereof, what is claimed is:

1. A method of determining the amount of glycol in an aqueous solution consisting essentially of:
    (a) providing a container containing a mixture of potassium dichromate, a catalyst comprised of mercuric sulfate and silver sulfate and a non-complexing acid;
    (b) adding a controlled volume of an aqueous solution containing glycol to said container to provide a mix;
    (c) permitting said mix a time sufficient to change color, said time not being in excess of 15 minutes; and
    (d) comparing said color to a set of color standards to determine the presence of glycol in said aqueous solution.

2. The method in accordance with claim 1 wherein the mixture contains 0.0001 to 20 wt. % potassium dichromate.

3. The method in accordance with claim 1 wherein the mixture contains 0.001 to 3.2 wt. % mercuric sulfate.

4. The method in accordance with claim 1 wherein the mixture contains 0.0001 to 6 wt. % silver sulfate.

5. The method in accordance with claim 1 wherein the mixture contains:
    0.0001 to 20 wt. % potassium dichromate;
    0.001 to 3.2 wt. % mercuric sulfate; and
    0.0001 to 6 wt. % silver sulfate.

6. The method in accordance with claim 1 wherein the mixture contains:
    0.02 to 20 wt. % potassium dichromate;
    0.01 to 2 wt. % mercuric sulfate; and
    0.001 to 3 wt. % silver sulfate.

7. The method in accordance with claim 1 wherein the acid is sulfuric acid.

8. The method in accordance with claim 1 wherein the acid is sulfuric acid having a concentration in the range of 40 to 98 wt. %.

9. The method in accordance with claim 1 wherein the mixture contains:
    0.0025 to 0.25 wt. % potassium dichromate;
    0.001 to 2 wt. % mercuric sulfate; and
    0.001 to 3 wt. % silver sulfate when the aqueous solution contains 30 to 150 ppm glycol.

10. The method in accordance with claim 1 wherein the mixture contains:
    0.25 to 1 wt. % potassium dichromate;
    0.001 to 5 wt. % mercuric sulfate; and
    0.001 to 6 wt. % silver sulfate when the aqueous solution contains 150 to 1500 ppm glycol.

11. A method of determining the presence of glycol in an aqueous solution comprising:
    (a) providing a container containing a test solution comprised of:
        0.0001 to 20 wt. % potassium dichromate;
        0.001 to 3.2 wt. % mercuric sulfate;
        0.001 to 6 wt. % silver sulfate, the balance sulfuric acid having a concentration in the range of 40 to 99 wt. %;
    (b) adding a controlled volume of aqueous solution containing glycol to said container to provide a mix having 0.25 to 10 parts test solution to one part aqueous solution containing glycol;
    (c) permitting said mix a time sufficient to change color, said time not being in excess of 10 minutes; and
    (d) comparing said color to a set of color standards to determine the presence of glycol in said aqueous solution.

12. A method of determining the presence of glycol in an aqueous solution comprising:
    (a) providing a container containing a test solution comprised of:
        0.02 to 20 wt. % potassium dichromate;
        0.001 to 2 wt. % mercuric sulfate;
        0.001 to 3 wt. % silver sulfate, the balance sulfuric acid having a concentration in the range of 70 to 99 wt. %;
    (b) adding a controlled volume of aqueous solution containing glycol to said container to provide a mix having 0.25 to 5 parts test solution to one part aqueous solution containing glycol;
    (c) permitting said mix a time sufficient to change color, said time not being in excess of 5 minutes; and
    (d) comparing said color to a set of color standards to determine the presence of glycol in said aqueous solution.

13. A method of determining the presence of glycol in an aqueous solution in the range of about 30 to 150 ppm glycol comprising:
    (a) providing a container containing a test solution comprised of:
        0,025 to 0.25 wt. % potassium dichromate;
        0.001 to 2 wt. % mercuric sulfate;
        0,001 to 3 wt. % silver sulfate, the balance sulfuric acid having a concentration of 40 to 99 wt. %;
    (b) adding a controlled volume of aqueous solution containing glycol to said container to provide a mix having 0.25 to 5 parts test solution to one part aqueous solution containing glycol;
    (c) permitting said mix a time sufficient to change color, said time not being in excess of 5 minutes; and
    (d) comparing said color to a set of color standards to determine the presence of glycol in said aqueous solution.

14. A method of determining the presence of glycol in an aqueous solution in the range of about 150 to 1500 ppm glycol comprising:
    (a) providing a container containing a test solution comprised of:
        0.25 to 1 wt. % potassium dichromate;
        0.001 to 5 wt. % mercuric sulfate;
        0.001 to 6 wt. % silver sulfate, the balance sulfuric acid having a concentration in the range of 40 to 99 wt. %;
    (b) adding a controlled volume of aqueous solution containing glycol to said container to provide a mix having 0.25 to 5 parts test solution to one part aqueous solution containing glycol;
    (c) permitting said mix a time sufficient to change color, said time not being in excess of 5 minutes; and
    (d) comparing said color to a set of color standards to determine the presence of glycol in said aqueous solution.

15. The method in accordance with claim 14 wherein the sulfuric acid concentration is in the range of 60 to 99 wt. %.

16. The method in accordance with claim 14 wherein the sulfuric acid concentration is in the range of 80 to 99 wt. %.

* * * * *